United States Patent [19]

Zwick

[11] Patent Number: 4,777,947
[45] Date of Patent: Oct. 18, 1988

[54] ENDOCERVICAL CURETTE

[75] Inventor: Roland J. Zwick, 897 Altos Oaks Dr., Los Altos, Calif. 94022

[73] Assignee: Roland J. Zwick, Inc., Mountain View, Calif.

[21] Appl. No.: 910,538

[22] Filed: Sep. 23, 1986

[51] Int. Cl.⁴ .............................................. A61B 17/22
[52] U.S. Cl. ...................... 128/304; 128/757
[58] Field of Search ............... 128/304, 757, 305, 312, 128/313, 758, 749

[56] References Cited

U.S. PATENT DOCUMENTS

| | | | |
|---|---|---|---|
| 2,715,899 | 8/1955 | MaClean | 128/304 |
| 3,308,825 | 3/1967 | Cruse | 128/757 |
| 3,774,612 | 11/1973 | Marco | 128/304 |
| 3,831,585 | 8/1974 | Brondy et al. | 128/757 |
| 3,857,384 | 12/1974 | Watson | 128/304 |
| 3,886,943 | 6/1975 | Skiff et al. | 128/304 |
| 4,340,066 | 7/1982 | Shah | 128/304 |

FOREIGN PATENT DOCUMENTS 158984 11/1963 U.S.S.R. ............................. 128/757

OTHER PUBLICATIONS

Sklar Surgical Instruments, 18th Ed., 1973.

Primary Examiner—C. Fred Rosenbaum
Assistant Examiner—Gene B. Kartchner
Attorney, Agent, or Firm—Flehr, Hohbach, Test, Albritton & Herbert

[57] ABSTRACT

An endoservical curette is disclosed which has a detachable tip portion which includes a scraper for removing tissue from the cervical canal and a well for retaining the tissue. The tip portion is secured to a shaft portion when in use to collect tissue and then detached from the shaft before being sent to a laboratory for analysis of the collected tissue.

1 Claim, 1 Drawing Sheet

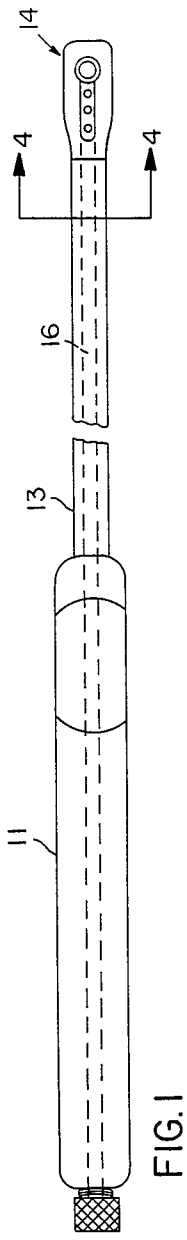
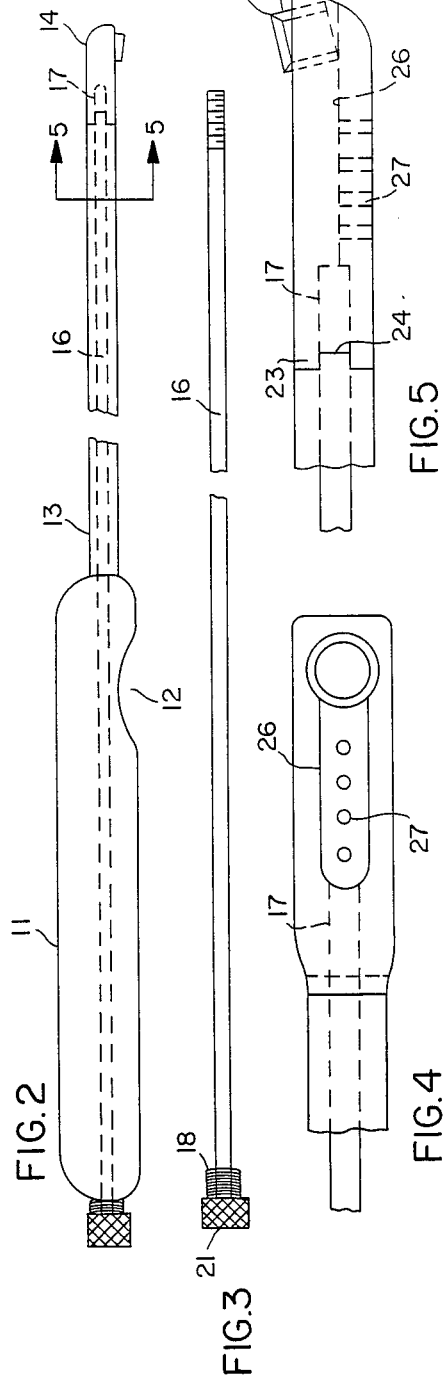
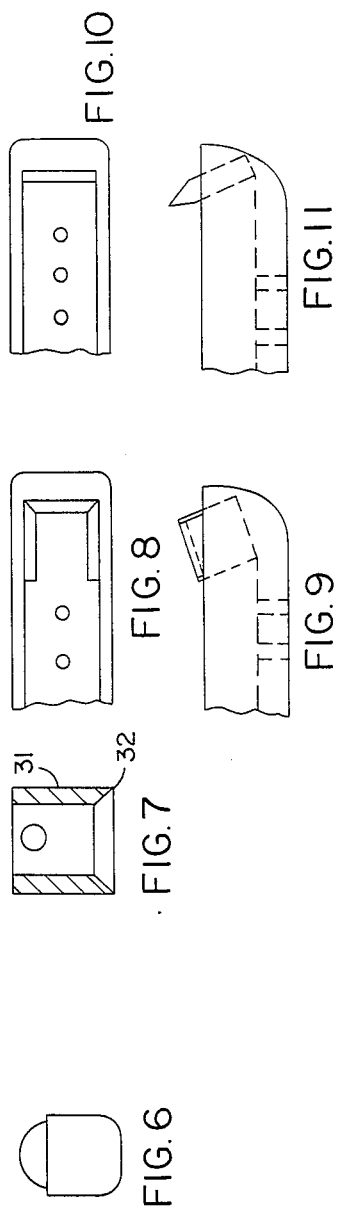

ENDOCERVICAL CURETTE

This invention relates generally to endocervical curettes and more particularly to an endocervical curette having a disposable tip.

Prior endocervical curettes are of many styles and shapes. They are designed to obtain tissue sample from the endocervical canal by scraping the outer cellular layer of the canal. Tissue is removed from the curette and placed on a sample surface for laboratory diagnosis. In general, curettes include a sharpened edge or tissue sampling surface formed integral with an elongated shank or shaft. A handle is secured to the other end of the shaft. In practice the curettes are sterilized and reused. As a result of repetitive uses, the blade or tissue sampling surface becomes dull and ineffective for scraping. When dulled they may cause patient discomfort and poor sample retrieval.

It is an object of the present invention to provide an improved endocervical curette.

It is another object of the present invention to provide an endocervical curette in which the blade or sampling surface is part of a disposable tip.

The foregoing and other objects of the invention are achieved by an endocervical curette in which a shank removably supports a disposable plastic tip provided with a sampling blade or surface.

The foregoing and other objects of the invention will be more clearly understood from the following description taken in conjunction with the drawings, of which:

FIG. 1 is a top plan view, partly broken away, of a curette in accordance with the present invention.

FIG. 2 is a side elevational view of the curette shown in FIG. 1.

FIG. 3 is a plan view of a tip retaining rod.

FIG. 4 is an enlarged view of the end of the curette taken along the line 4—4 of FIG. 1 showing the disposable tip in more detail.

FIG. 5 is an enlarged view of the end of the curette taken along the line 5—5 of FIG. 2, showing the disposable tip in more detail.

FIG. 6 is an end elevational view of the disposable tip.

FIG. 7 is an enlarged sectional view of a suitable scraping blade.

FIG. 8 is a top plan view of a portion of another tip having a scraper blade of different design.

FIG. 9 is a side elevational view of the portion of the disposable tip shown in FIG. 8.

FIG. 10 is a top plan view of a disposable tip including a flat blade.

FIG. 11 is a side elevational view of the tip shown in FIG. 10.

Referring to FIGS. 1 and 2, the curette includes a handle 11 having a thumb depression 12 with an elongated hollow shaft or shank 13. A disposable tip 14 is secured to the end of the shaft by a threaded rod 16, FIG. 3, shown in dotted line in FIGS. 1 and 2. The threaded rod extends through the handle and through the hollow shaft 13 to engage the threaded well 17 formed in the tip. Preferably, the rod is spring-loaded by a spring 18 which is compressed between the knurled knob 21 and the end of the handle. To prevent rotation of the tip on the shaft, the disposable tip and end of the shaft are provided with cooperating notches and protrusions 23,24 which mate as shown in FIGS. 2 and 5.

The disposable tip is preferably molded from high strength plastic and includes a well 26 with holes or openings 27 extending through the bottom wall. A blade 31 is embedded in the end of the plastic tip. In this embodiment the blade comprises a cylindrical member which is machined at one end to form sharp cutting edges 32. The blade includes an opening 33 which communicates with the well 26 whereby tissue and mucous collected by scraping of the blade enter the cup and flow through the opening 33 into the well 26. Mucous and liquid may escape through the bottom openings 27 with the tissue retained in the well 26 and cup formed by the cylindrical member. The tip is then removed and sent to the laboratory where the tissue is tested and disposed of. A new tip is inserted by threadibly engaging the rod with the tip.

It is apparent that other types of scraping blades may be used. For example, in FIG. 8 and 9, a U-shaped scraping blade is shown with the open end communicating with the well. In FIGS. 10 and 11 a straight blade is shown communicating with the well.

Thus, there has been provided an improved endocervical curette which uses replaceable pre-sharpened tips. The pre-sterilized disposable tips are for one-time use only.

What is claimed is:

1. An endocervical curette comprising a handle, a hollow shaft having one end secured to said handle and the other end including notches and protrusions, a disposable tip having an end with notches and protrusions for engaging the other end of said shaft and a threaded hole, said tip including a scraper for removing tissue and a well for receiving and retaining scraped tissue, a rod extending through said handle and shaft with one end extending beyond said shaft, said one end being threaded to threadably engage said tip and hold the same in engagement with the other end of said shaft to prevent rotation of the tip with respect to the shaft to permit said tip with retained tissue to be released by unthreading the rod.

* * * * *